United States Patent [19]

Maguire

[11] 4,159,650

[45] Jul. 3, 1979

[54] WELD TESTING APPARATUS

[75] Inventor: Roy L. Maguire, Edelstein, Ill.

[73] Assignee: Caterpillar Tractor Co., Peoria, Ill.

[21] Appl. No.: 909,758

[22] Filed: May 26, 1978

[51] Int. Cl.² .................................................. G01N 3/22
[52] U.S. Cl. .................................................. 73/847
[58] Field of Search .................. 73/847, 848, 841, 843, 73/850

[56] References Cited

U.S. PATENT DOCUMENTS

| 2,908,162 | 10/1959 | Kalbow | 73/848 |
| 3,839,905 | 10/1974 | McCallen | 73/848 |

FOREIGN PATENT DOCUMENTS 164692  1/1965  U.S.S.R. ............................ 73/847

Primary Examiner—Jerry W. Myracle
Attorney, Agent, or Firm—Frank L. Hart

[57] ABSTRACT

A welded assembly has first and second portions connected one to the other by welds about a common axis. Testing apparatus holds one of the portions against rotation about the axis and controllably exerts a torquing force of a preselected magnitude on the other portion. The torquing force is exerted about the axis and oriented relative to the welds for exerting a radial force through each of said welds. Application of the torquing force and radial forces provides nondestructive testing of the welded assembly and of the welds of the assembly, respectively.

6 Claims, 2 Drawing Figures

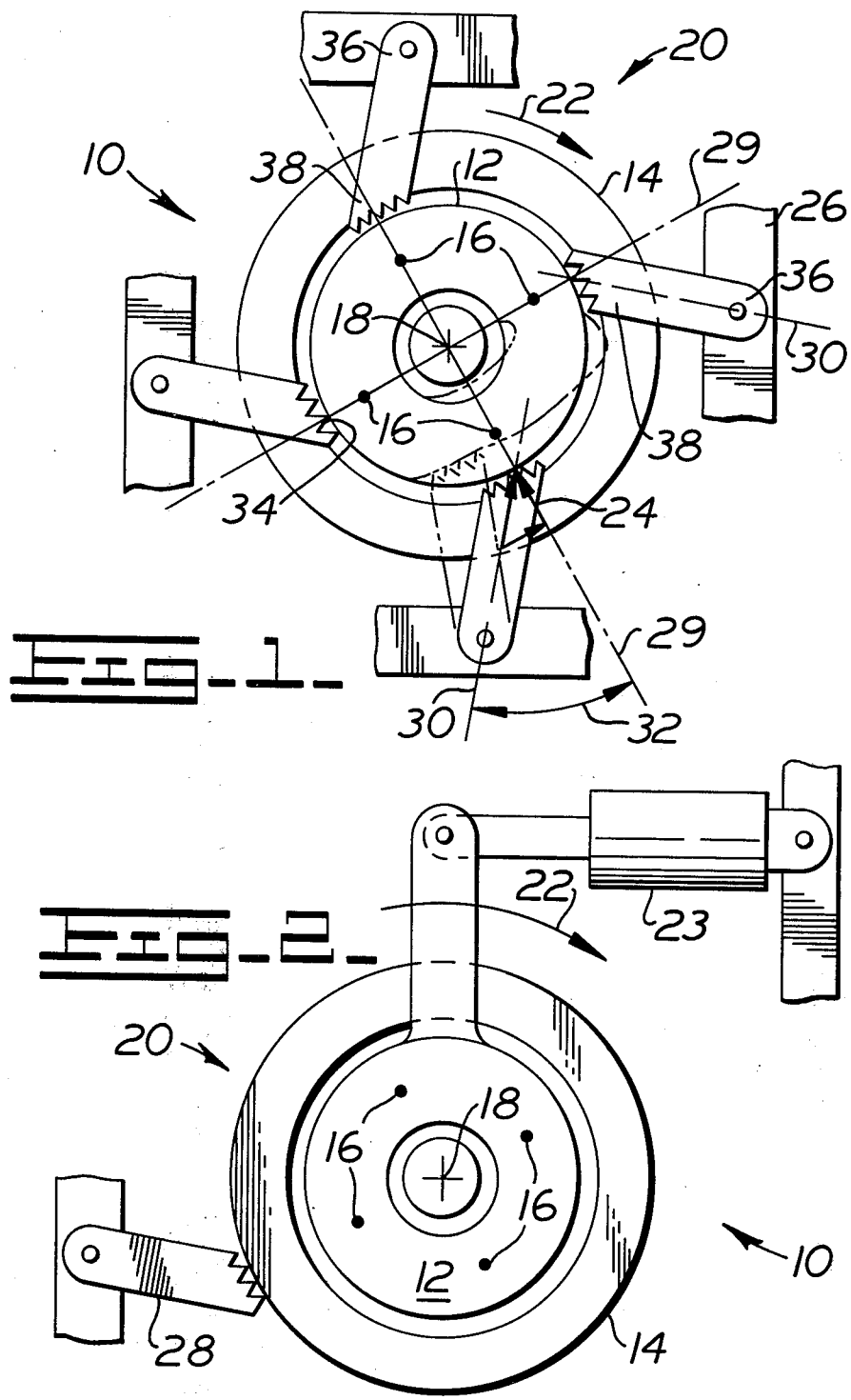

4,159,650

WELD TESTING APPARATUS

BACKGROUND OF THE INVENTION

In the use of a welded assembly, it is desirable to nondestructively test the assembly and the welds connecting the portions of the assembly one to the other.

Commonly, the portions of said assemblies are spot welded or projection welded one to the other. For example, such a welded assembly typically consists of a thrust bearing projection welded to a retainer portion. It is desirable to test the retainer assembly under operational load and to test the individual projection welds for a minimum shear strength.

The welded assembly can be nondestructively tested by application of a torque simulating its operational load. However, to test the welds of an assembly having greater than one projection weld, the welded assembly heretofore has been divided into portions, each containing one weld. A force is then applied to each weld until the weld fails in order to determine the minimum shear strength of that weld. The resultant destruction of the welded assembly represents a waste of time and labor.

Therefore, it is desirable to provide means for controllably exerting a force on a welded assembly to nondestructively test the welded assembly and each weld of the assembly.

SUMMARY OF THE INVENTION

According to the present invention, a welded assembly has first and second portions connected one to the other by welds about a common axis. Means is provided for holding one of the portions against rotation about said axis and for controllably exerting a torquing force of a preselected magnitude on the other portion. The torquing force is exerted about the common axis and oriented relative to the welds for exerting a radial force through each of said welds for nondestructively testing the welded assembly and each weld of the assembly.

BRIEF DESCRIPTION OF THE DRAWINGS

FIG. 1 is a diagrammatic view of an embodiment of the invention being used to test a welded assembly.

FIG. 2 is a diagrammatic view showing application of the torquing force to a portion of the welded assembly.

DETAILED DESCRIPTION

Referring to the drawings, a welded assembly 10 has first and second portions 12,14 connected one to the other by welds 16 about a common axis 18. Means 20 is provided for holding one of the portions 12,14 against rotation about the common axis 18 and for controllably exerting a torquing force 22 of a preselected magnitude on the other portion 14,12. Said torquing force 22 is exerted about the axis 18 and is oriented relative to the welds 16 for exerting a radial force 24 through each of said welds 16. As shown in FIG. 2, the torquing force 22 is exerted about said axis 18 by a fluid cylinder 23. The torquing force 22 can also be exerted by other means as is known in the art.

The means 20 includes a frame 26 and arm 28. As is shown, the means 20 preferably has a plurality of arms 28. The arms 28 each have first and second end portions 36,38 and are pivotally connected at respective first end portions 36 to the frame 26. The respective second end portions are each in contact with the other portion 14,12 of the welded assembly portion 10 at a location immediately adjacent respective welds 16.

Each of the welds 16 has a center line 29 passing through the center of each weld 16 and perpendicular to and intersecting the common axis 18 of the welds 16. Each arm 28 has a longitudinal axis 30. The radial force 24 is exerted through each of said welds 16 when the longitudinal axis 30 of a respective arm 28 defines an acute angle 32 with a respective weld center line 29.

It is desirable that the second end portion 38 of each arm 28 have means 34 for resisting rotation of the welded assembly 10 in response to exerting said torquing force 22 on one of the portions 12,14 of the welded assembly 10. Preferably, said resisting means 34 is a plurality of serrations positioned about the second end portion 38 of each arm 28 and in contact with the respective one of the portions 12,14 of the assembly 10.

Operation

In the operation of the weld testing apparatus, the arms 28 hold one of the first and second portions 12,14 of the welded assembly 10 against the torquing force 22. Therefore, the arms 28 exert a radial force 24 through respective welds 16. The torquing force 22 tests the assembly 10 as a unit and respective radial forces 24 test each weld 16 individually.

The first portion 12 of the welded assembly 10 is a thrust bearing 12 projection welded to the second portion or retainer 14. Such thrust bearing welded assemblies are well known in the art and are commonly used to position track rollers on roller shafts. As is shown in FIG. 1, the testing apparatus 20 is of a construction sufficient for holding the thrust bearing 12 against rotation about the common axis 18 and for controllably exerting the torquing force 22 on the retainer portion 14. However, the first portion 12 can be the retainer 14 and said testing apparatus 19 can be constructed to test a welded assembly 10 of this configuration (FIG. 2).

To test the assembly 10 at specific loads, a torquing force 22 of predetermined magnitude is exerted about the axis 18. To test each weld 16, the radial forces 24 are adjusted to specific magnitudes by varying the angles 32 of the arms 28.

During exertion of the torquing force 22 on the welded assembly 10, the serrations 34 resist the tendency of the thrust bearing portion 14 to rotate. In this manner, a radial force 24 is exerted through each weld 16. The assembly 10 can satisfactorily resist the torquing force 22 and contain a defective weld. However, as is shown on outline in FIG. 1, the radial force 24 exerted through the defective weld causes distortion of the bearing portion 12 adjacent the defective weld (shown in outline). Therefore, an individual defective weld is detected.

Other aspects, objects and advantages of this invention can be obtained from a study of the drawings, the disclosure and the appended claims.

The embodiments of the invention in which an exclusive property or privilege is claimed are defined as follows:

1. A testing apparatus for testing a welded assembly having first and second portions connected one to the other by welds about a common axis, comprising:

means for holding one of the portions against rotation about said axis and for controllably exerting a torquing force of a preselected magnitude on the other portion, said torquing force being about said axis and oriented relative to said one of the portions for controllably exerting a radial force component of a preselected magnitude through each of said welds.

2. A testing apparatus, as set forth in claim 1, wherein said means includes:

a frame; and an arm having first and second end portions and being pivotally connected at the first end portion to the frame, said second end portion being in contact with said other portion of the welded assembly at a location immediately adjacent a respective one of the welds.

3. A welded assembly, as set forth in claim 2, wherein each of the welds has a center line perpendicular to and intersecting the common axis of said welds and said arm has a longitudinal axis, said arm longitudinal axis defining an acute angle of predetermined magnitude with the related one of said weld center lines.

4. A testing apparatus, as set forth in claim 2, wherein said second end portion of the arm has means for resisting rotation of the welded assembly in response to exerting said torquing force on one of the portions of the welded assembly.

5. A testing apparatus, as set forth in claim 4, wherein said resisting means includes a plurality of serrations positioned about said second end portion of the arm and in contact with the associated portion of the welded assembly.

6. A testing apparatus, as set forth in claim 1, wherein said testing apparatus is of a construction sufficient for holding one portion and for controllably exerting said torquing force on the other portion of a retainer and thrust bearing welded assembly.

* * * * *